United States Patent [19]  [11]  4,238,617
Bortnick  [45]  Dec. 9, 1980

[54] CYANIDE PROCESS FOR THE PREPARATION OF 4H-1,2,4-TRIAZOLES

[75] Inventor: Newman Bortnick, Oreland, Pa.

[73] Assignee: Rohm and Haas Company, Philadelphia, Pa.

[21] Appl. No.: 43,295

[22] Filed: May 29, 1979

[51] Int. Cl.$^3$ .............................................. C07D 249/08
[52] U.S. Cl. ..................................................... 548/262
[58] Field of Search ...................... 260/308 R; 548/262

[56] References Cited
PUBLICATIONS

Elderfield, Heterocyclic Compounds, vol. 7, (New York, 1961), pp. 435–436.
Smith, Open-chain Nitrogen Compounds, vol. 1, (W. A. Benjamin, Inc., New York, 1965), pp. 180, 213–214.
Rusanov, Russian Chemical Reviews, vol. 43, pp. 795–804 (1974).

Primary Examiner—Alton D. Rollins

[57] ABSTRACT

This invention relates to a novel process for the preparation of 4H-substituted-1,2,4-triazoles. In this process, 4H-substituted-1,2,4-triazoles are prepared by the reaction of an amine with hydrazine and a nitrile.

9 Claims, No Drawings

CYANIDE PROCESS FOR THE PREPARATION OF 4H-1,2,4-TRIAZOLES

BACKGROUND OF THE INVENTION

Certain 4H-substituted-1,2,4-triazoles such as Indar ® fungicide are known to possess fungicidal activity. Indar ® fungicide, 4H-n-butyl-1,2,4-triazole is particularly effective against wheat leaf rust. This activity is reported in *Science*, Vol. 169, pages 997 and 998, Sept. 4, 1970 by William C. von Meyer. Various methods for preparing 4H-substituted-1,2,4-triazoles have been reviewed in K. T. Potts' article in "*Chemical Reviews*" Vol. 61, pages 87 to 127, 1961; in R. K. Bartlett and I. R. Humphrey's article in "*Journal of the Chemical Society*" (London) page 1664 to 1666, 1967; in "*Chemical Abstracts*" Vol. 77, 34431w, 1972; in "*Chemical Abstracts*" Vol. 77, 34426y, 1972 and in "*Chemical Abstracts*" Vol. 85, 123928w, 1976. An article in "*Russian Chemical Reviews*", Vol. 43 (9), page 795 to 804, 1974 by A. L. Rusanov discloses the preparation of 4H-amino-1,2,4-triazoles by the reaction of 2 moles of a substituted nitrile with one mole of hydrazine.

The current process for the production of 4H-n-butyl-1,2,4-triazole, a commercial fungicide sold by Rohm and Haas Company under the trademark Indar ® utilizes a three step process wherein the triazole ring carbon atoms are derived from methyl formate and triethyl orthoformate. In this process formylhydrazine is formed from hydrazine hydrate and methyl formate. This formylhydrazine is then reacted in situ with triethyl orthoformate to give N-ethoxymethylene-N'-formylhydrazine. Addition of n-butylamine followed by heating for several hours produces high purity 4H-n-butyl-1,2,4-triazole in better than 70% yields. The major difficulty with this process is that the final product obtained has a relatively high net selling price. This is due primarily to unusually high raw material costs which, in turn, are a direct result of the inefficient use of the expensive starting material, triethyl orthoformate as the source of one of the carbon atoms of the triazole ring. This reagent alone accounts for about 50% of the total raw material costs for this product. This is due to the fact that less than 10% of the weight of the triethyl orthoformate initially charged ends up in the final product. Thus there is a need to reduce both the raw material cost and the net selling price for the manufacture of 4H-substituted 1,2,4-triazoles by replacing triethyl orthoformate with a more efficient and less expensive reagent to provide the source of the triazole ring carbon atoms. The process of the present invention meets these requirements and further allows for symmetrical substitution in the 3 and 5 positions of the triazole ring.

SUMMARY OF THE INVENTION

The present invention relates to a novel one-step process for the preparation of 4-substituted-1,2,4-triazoles of the formula

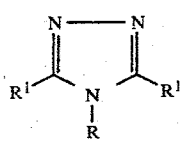

wherein one mole of hydrazine is reacted with about one mole or an excess amount of a substituted amine of the formula $$R-NH_2 \quad (II)$$

wherein R is alkyl, alkenyl, optionally substituted aryl or optionally substituted aralkyl, and about 2 moles or an excess amount of a nitrile of the formula $$R^1CN \quad (III)$$

wherein $R^1$ is hydrogen, alkyl, optionally substituted aryl or optionally substituted aralkyl to form a 4H-substituted-1,2,4-triazole wherein the nitrile furnishes both ring carbon atoms and the 3,5 substituents and the 4 substituent of the triazole is derived from the substituted amine used as the starting material. This reaction is carried out at relatively low temperatures, produces high yields and allows for great variability in the 4H-substituent of the 1,2,4-triazole product and further allows for symmetrical substitution in the 3 and 5 positions of the 4H-1,2,4-triazole ring.

DETAILED DESCRIPTION OF THE INVENTION

This invention relates to a novel one step process for the preparation of 4H-substituted-1,2,4-triazoles of the formula

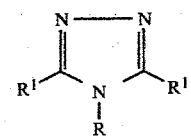

wherein R is selected from the group consisting of alkyl, alkenyl, optionally substituted aryl and optionally substituted aralkyl, and $R^1$ is selected from the group consisting of hydrogen, alkyl, optionally substituted aryl or optionally substituted aralkyl, which comprises reacting one mole of hydrazine with about one mole or an excess amount of an amine of Formula (II) wherein R is as defined above, and about two moles or an excess amount of a nitrile of Formula (III) wherein $R^1$ is as defined above, at temperatures from about room temperature up to about 250° C., and when $R^1$ is hydrogen up to about 100° C., either neat or in the presence of an inert solvent, and optionally in the presence of an acid catalyst.

In the definition of the substituents R and $R^1$ as used in the specifications and claims, the term "optionally substituted" as applied to the aryl or aralkyl substituents is meant to include aryl or aralkyl groups which may be unsubstituted or substituted in the aryl ring with up to three substituents selected from the group consisting of halogen, nitro, trifluoromethyl, ($C_1$-$C_4$)alkyl, ($C_1$-$C_4$)alkoxy, carbamoyl, carboxy, and the like unless specifically defined otherwise.

Amines of Formula (II) that can be utilized in the process of this invention include ($C_1$-$C_{20}$) alkylamine, ($C_2$-$C_{10}$) alkenylamine, unsubstituted aniline, benzylamine or phenethylamine or aniline, benzylamine or phenethylamine the aryl portion of which is substituted with up to three substituents selected from the group consisting of halogen, nitro, trifluoromethyl, ($C_1$-$C_4$) alkyl, ($C_1$-$C_4$) alkoxy, carbamoyl, carboxy, and the like and when R is benzyl or phenethyl the carbon atom of the alkyl chain adjacent to the aryl ring can be substituted with up to two substituents independently selected from the group consisting of cyano, ($C_1$-$C_{10}$) alkyl, ($C_1$-$C_{10}$) alkoxy, ($C_2$-$C_{10}$) alkenoxy, phenyl or benzyl or phenyl or benzyl the aryl portion of which is substituted with up to three substituents selected from the group consisting of halogen, nitro, trifluoromethyl, ($C_1$-$C_4$) alkyl, ($C_1$-$C_4$) alkoxy, carbamoyl and carboxy.

Typical examples of amines that can be utilized in this invention include methylamine, ethylamine, propylamine, propylamine, n-butylamine, isobutylamine, sec-butylamine, tert-butylamine, pentylamine, hexylamine, cyclohexylamine, heptylamine, octylamine, 3,3,5-trimethylpentylamine, nonylamine, 3,3,5-trimethylcyclohexylmethylamine, decylamine, dodecylamine, hexadecylamine, octadecylamine, eicosylamine, isobornylamine, bornylamine, allylamine, 3,4-cyclohexenylamine, Δ2,3-decenylamine, Δ7,8-pentadecenylamine, Δ9,10-eicosenylamine, aniline, 2,4-dichloroaniline, 3,5-dimethylaniline, 2-nitroaniline, 3,5-difluoroaniline, 2,4-di-n-butylaniline, 2,4-dimethoxyaniline, 2-chloro-4-trifluoromethylaniline, 2,6-dimethylaniline, benzylamine, 2,4-dichlorobenzylamine, 4-chlorobenzylamine, 2,4-dichlorophenethylamine, 4-chlorophenethylamine, β-n-butylphenethylamine, β-n-butyl-2,4-dichlorophenethylamine, β-n-butyl-β-cyano-phenethylamine, β-n-butyl-β-cyano-2,4-dichlorophenethylamine.

The nitriles of Formula (III) that can be utilized in the process of this invention include hydrogen cyanide, alkanonitriles optionally substituted aryl cyanides and optionally substituted aralkanonitriles preferably nitriles wherein $R^1$ is selected from the group consisting of halogen, ($C_1$-$C_{10}$) alkyl, unsubstituted phenyl or benzyl or phenyl or benzyl the aryl portion of which is substituted with up to three substituents selected from the group consisting of halogen, nitro, trifluoromethyl, ($C_1$-$C_4$) alkyl, ($C_1$-$C_4$) alkoxy, carbamoyl and carboxy.

Typical examples of the nitriles that can be utilized in this invention include hydrogen cyanide, acetonitrile, propionitrile, isobutyronitrile, cyclohexanecarbonitrile, capronitrile, decanonitrile, benzonitrile, 4-toluenitrile, 4-chlorobenzonitrile, 2,4-dichlorobenzonitrile, 3,5-dichlorobenzonitrile, 4-trifluoromethylbenzonitrile, 3-chloro-4-trifluoromethylbenzonitrile, 3-methoxybenzonitrile, phenylacetonitrile, 2,4-dichlorophenylacetonitrile.

The acidic catalysts which can be utilized in this invention include any hydrogen ion releasing materials having an acid strength equal to or stronger than that of ammonium chloride and would include crosslinked polymeric sulfonic acid resins capable of liberating hydrogen ions such as Amberlyst® 15, Amberlyst® XM-1010, and the like.

Typical examples of acid catalysts that can be utilized in this invention include hydrogen chloride, sulfuric acid, methanesulfonic acid, p-toluenesulfonic acid, phosphoric acid, polyphosphoric acid, and the ammonium or lower alkylammonium salts thereof.

The present process can be utilized to include 4H-substituted 1,2,4 triazoles wherein symmetrical substituents can be introduced into the 3 and 5 position of the 4H-1,2,4-triazole ring by the use of suitable nitriles of Formula (III) such as alkanonitriles, optionally substituted aryl cyanides and optionally substituted aralkanonitriles. However, the preferred process of this invention is directed to the use of hydrogen cyanide thus producing 4H-substituted-1,2,4-triazoles having no substituents in the 3 and 5 positions.

The preferred process of this invention utilizes an amine to hydrazine molar ratio of from about 1:1 to about 15:1, a nitrile to hydrazine molar ratio of from about 2:1 to about 5:1 and an acidic catalyst (hydrogen ion) to hydrazine molar ratio of from about 3:1 to about 1:20.

Although the reagents may be mixed in any order or may be individually added in any order, the most preferred method for performing the process of this invention involves the slow addition of hydrazine to the amine/hydrogen cyanide reaction mixture thereby obtaining a very low steady state hydrazine concentration which enables high amine to hydrazine ratios until near the end of the reaction when the total number of moles of hydrazine added begins to approach the total number of moles of amine initially present. Such a procedure would allow more nearly stoichiometric conditions overall while favoring the formation of the desired product. In addition thereto, the simultaneous addition of hydrazine and hydrogen cyanide to the amine can be utilized to favor the formation of the desired product.

The more preferred process of this invention involves the addition of a molar amount of hydrazine to at least a molar amount of an amine of the Formula (III), wherein R is as defined above and at least a 2 molar amount of hydrogen cyanide, in the presence of at least a molar amount of an acid catalyst, such as hydrogen chloride or ammonium chloride, at temperatures from about 50° C. to about 100° C.

Alternatively, the amine and ammonium chloride are first mixed together and after ammonia evolution has ceased, hydrazine or an aqueous solution of hydrazine (down to about 50% aqueous hydrazine) is then added with vigorous stirring. The hydrogen cyanide is then added slowly into the reaction mixture, the exotherm being controlled at about 50° C. by the rate of addition of the hydrogen cyanide. After completion of the hydrogen cyanide addition, the temperature is increased to about 75° C. and maintained at this temperature. After about a total of 5 hours, the reaction is complete in about 90% yield and the product can be utilized as is or further purified by standard techniques.

Utilizing the procedures as disclosed above, the following data were generated which further illustrates the latitude of the parameters which can be utilized in accordance with the process of the present invention. These data are not to be interpreted as establishing limitations on the breadth and scope of this invention but is merely provided to exemplify the process of the present invention.

EXAMPLE 1

Into a 250 ml four-necked flask equipped with a thermometer, a rubber septum, a condenser (<10° C.), and a pressure equalizing volumetric delivery funnel were placed ammonium chloride (21.0 g, 0.39 moles) and n-butylamine (150 ml, 1.57 moles). To this was added, after ammonia evolution had ceased, 54% aqueous hydrazine (8.5 ml, 0.14 moles) and the mixture was stirred vigorously. Hydrogen cyanide (20 ml, 0.51 moles) was transferred directly from the HCN tank to the delivery funnel via a flexible line and was allowed to drop slowly into the reaction mixture. During the addition the temperature increased to about 50° C. After completion of the hydrogen cyanide addition, the temperature was increased to 75° C. Some refluxing was observed during the first hour. After a total of five hours the reaction appeared complete. NMR and GC analyses of the dark red product mixture indicated formation of 4-n-butyl-1,2,4-triazole in a yield of 90% based on hydrazine.

EXAMPLE 2

Utilizing conditions similar to Example 1, an approximately stoichiometric mixture of n-butylamine, hydrazine, and hydrogen cyanide was reacted at 85° C. for one and a half hours to produce a 40% yield of 4-n-butyl-1,2,4-triazole. Although it is not known what the limiting yield would have been had this reaction been pursued to completion, it was clear from the NMR data that substantial by-product formation was occurring.

EXAMPLE 3

Example 3 was run using similar conditions but with a four-fold excess of butylamine. 4-n-butyl-1,2,4-triazole formed considerably more slowly in this experiment than in Example 2 as might be expected in view of the lower initial concentrations of HCN and hydrazine, but the rate of the by-product formation appeared to decrease more than the rate of 4-n-butyl-1,2,4-triazole formation. For this reason, it seems likely that continuing Example 3 beyond the 9.5 hours indicated in Table I would have resulted in a final 4-n-butyl-1,2,4-triazole yield substantially above the 40% value obtained in Example 2.

EXAMPLE 4

In Example 4 an attempt was made to increase the rate of 4-n-butyl-1,2,4-triazole formation over that observed in Example 3 while maintaining the same procedure and butylamine/hydrazine ratio by adding a small amount of $NH_4Cl$ as an acid catalyst. As Table I shows, after eleven hours at 75° C. a 52% yield of 4-n-butyl-1,2,4-triazole resulted. This is nearly double the yield obtained in Example 3 after nine and a half hours at the same temperature, clearly indicating a substantial increase in rate.

EXAMPLE 5

After mixing the butylamine and HCN and heating at 75°–85° C. for two hours the reaction mixture turned dark red-brown and became very viscous, suggesting that HCN polymerization had occurred. Reaction of this mixture with hydrazine did produce some 4-n-butyl-1,2,4-triazole.

EXAMPLE 6

In Example 6, Example 5 was repeated except that the butylamine-HCN mixture was not heated so as to avoid polymerizing the hydrogen cyanide. An NMR spectrum of this mixture gave no evidence of butylformamidine formation but rather was consistent with a simple solution of butylammonium cyanide in butylamine. Hydrazine was added and the reaction mixture was heated to 75° C. to give a 63% yield of 4-n-butyl-1,2,4-triazole in only four hours. The only differences between this experiment and Examples 3 and 4 were the order of the HCN—$H_2NNH_2$ additions and the amount of $NH_4Cl$ catalyst used; the former seems to have had no discernible effect while the latter is presumably responsible for the significant rate increase.

EXAMPLE 7

Example 7 was run using an approximately 6/1 butylamine/hydrazine ratio rather than the 4/1 ratio used in Example 6. As shown in Table I, the 4-n-butyl-1,2,4-triazole yield did increase by ten percent to 66%. While this result is strongly indicative, it cannot be considered conclusive in view of the limited accuracy of the NMR method used to calculate the yields.

EXAMPLE 8

An attempt to investigate this question was made in Example 8. In this case the butylamine/hydrazine ratio was increased to 11/1 resulting in a final yield of 90% after five hours at 75° C. This is a substantial increase over the 60% yield obtained in Example 6 and clearly demonstrates the sensitivity of the yield to the butylamine/hydrazine ratio.

EXAMPLE 9

In Example 9, hydrogen cyanide and hydrazine were added in small increments to butylamine at 75° C. Unfortunately, experimental problems led to the loss of hydrogen cyanide from the reaction mixture during the experiment making it likely that the final yield of 46% listed in Table I represents the limited availability of HCN rather than the maximum yield achievable by the method.

EXAMPLE 10

The $NH_4Cl$ normally used as the acid catalyst was replaced by Amberlyst ® 15 resin. A 50% of 4-n-butyl-1,2,4-triazole was obtained after 11.5 hours at 75° C. A comparison of the rate of 4-n-butyl-1,2,4-triazole formation in this experiment with that observed in Examples 3 (no acid) and 4 (0.2 molar acid). Amberlyst 15 ® does catalyze the HCN reaction, but not as effectively on an equivalent to equivalent basis as hydrogen chloride.

EXAMPLE 11

Example 11 was carried out using acetonitrile rather than hydrogen cyanide. The molar ratio of reactants was essentially the same as that used in Example 6. After 19 hours at 75°–80° C. an approximately 20% yield of 4-butyl-3,5-dimethyl-1,2,4-triazole was obtained.

Table I summarizes the reaction conditions and 4-n-butyl-1,2,4-triazole yields for a series of experiments in which 4-n-butyl-1,2,4-triazole was formed by the direct reaction of n-butylamine, hydrazine, and hydrogen cyanide. In these experiments, no attempt was made to obtain accurate data concerning yields, conversions, mass balances, or rates in most cases. However, the results presented in Table I are believed to be correct to within ±10%.

TABLE I

| Example Number | Moles | | | | [H+] (Moles/l) | T(°C.) | Time (Hours) | % Yield[4] |
|---|---|---|---|---|---|---|---|---|
| | $BuNH_2$ | $H_2NNH_2$ | HCN | $NH_4Cl$ | | | | |
| 1 | 1.05 | 0.25 | 0.51 | | | 25 | 70 | Small |
| 2 | 0.58 | 0.51 | 1.02 | | | 85 | 1.5 | 40 |
| 3 | 1.05 | 0.25 | 0.51 | | | 75 | 9.5 | 28 |
| 4 | 1.05 | 0.25 | 0.51 | 0.026 | 0.2 | 75 | 11 | 52 |
| 5 | 1.05 | 0.25 | 0.51 | 0.25 | 2.0 | 75 | 1.5 | Small |

TABLE I-continued

| Example Number | Moles BuNH$_2$ | Moles H$_2$NNH$_2$ | Moles HCN | Moles NH$_4$Cl | [H+] (Moles/l) | T(°C.) | Time (Hours) | % Yield[a] |
|---|---|---|---|---|---|---|---|---|
| 6 | 1.05 | 0.25 | 0.51 | 0.25 | 2.0 | 75 | 4 | 60 |
| 7 | 1.57 | 0.25[b] | 0.61 | 0.25 | 1.3 | 75 | 4 | 66 |
| 8 | 1.57 | 0.14[c] | 0.51 | 0.39 | 2.2 | 75 | 5 | 90 |
| 9 | 1.05 | 0.25[b] | 0.61 | 0.25 | 1.9 | 75 | 9 | 46 |
| 10 | 1.05 | 0.25 | 0.51[d] | | 0.4[e] | 75 | 11.5 | 50 |
| 11 | 1.05 | 0.25 | 0.52[f] | 0.25 | | 75 | 19 | 20[g] |

[a]Based on hydrazine
[b]85% aqueous hydrazine
[c]54% aqueous hydrazine.
[d]10 g of Amberlyst® 15 resin was added as catalyst instead of NH$_4$Cl.
[e]Assuming 5 meq. H+/g of resin.
[f]CH$_3$CN used instead of HCN.
[g]Of 4H-butyl-3,5-dimethyl-1,2,4-triazole.

It is to be understood that obvious modifications of the conditions employed in the process of the present invention, are deemed to be incorporated into this specification and are meant to be encompassed by the claims appended hereto.

I claim:
1. A process for the preparation of a 4H-1,2,4-triazole of the formula

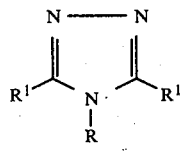

wherein
R is selected from the group consisting of (C$_1$–C$_{20}$) alkyl, (C$_2$–C$_{10}$) alkenyl, and phenyl, benzyl or phenethyl or phenyl, benzyl or phenethyl the aryl portion of which is substituted with up to three substituents selected from the group consisting of halogen, nitro, trifluoromethyl, (C$_1$–C$_4$) alkyl, (C$_1$–C$_4$) alkoxy, carbamoyl and carboxy and when R is benzyl or phenethyl the carbon atom of the alkyl chain adjacent to the aryl ring can be substituted with up to two substituents independently selected from the group consisting of cyano, (C$_1$–C$_{10}$) alkyl, (C$_1$–C$_{10}$) alkoxy, (C$_2$–C$_{10}$) alkenoxy, phenyl or benzyl or phenyl or benzyl the aryl portion of which is substituted with up to three substituents selected from the group consisting of halogen, nitro, trifluoromethyl, (C$_1$–C$_4$) alkyl, (C$_1$–C$_4$) alkoxy, carbamoyl, and carboxy and R$^1$ is selected from the group consisting of hydrogen, (C$_1$–C$_{10}$) alkyl, unsubstituted phenyl or benzyl or phenyl or benzyl substituted with up to three substituents selected from the group consisting of halogen, nitro, trifluoromethyl, (C$_1$–C$_4$) alkyl, (C$_1$–C$_4$) alkoxy, carbamoyl and carboxy,
which comprises
reacting
(a) one mole of hydrazine with
(b) about one mole or an excess amount of an amine of the formula

RNH$_2$ wherein
R is as defined above and
(c) about 2 moles or an excess amount of a nitrile of the formula

R$^1$CN wherein
R$^1$ is as defined above,
at temperatures from about room temperature to about 250° C., either neat or in the presence of an inert solvent, and optionally in the presence of an acid catalyst.

2. A process according to claim 1 wherein R is selected from the group consisting of (C$_1$–C$_{10}$) alkyl, unsubstituted phenyl, benzyl or phenethyl or phenyl, benzyl or phenethyl, the aryl portion of which is substituted with up to two halogen atoms and when R is benzyl or phenethyl the alkyl portion is independently substituted with up to two substituents independently selected from the group consisting of cyano, (C$_1$–C$_4$) alkyl, (C$_1$–C$_4$) alkoxy, (C$_2$–C$_4$) alkenoxy, phenyl or benzyl or phenyl or benzyl the aryl portion of which is substituted with up to two halogen atoms and R$^1$ is hydrogen.

3. A process according to claim 2 wherein said amine to hydrazine molar ratio is from about 1:1 to about 15:1, said nitrile to hydrazine molar ratio is from about 2:1 to about 5:1 and said acidic catalyst (hydrogen ion) to hydrazine molar ratio is from about 3:1 to about 1:20.

4. A process according to claim 3 wherein the hydrazine, the amine of the formula RNH$_2$, and the hydrogen cyanide are mixed together neat and then heated to about 100° C. in the presence of an acidic catalyst.

5. A process according to claim 4 wherein the acidic catalyst is hydrogen chloride.

6. A process according to claim 2 wherein the hydrazine is slowly added to the mixture of said amine and hydrogen cyanide at a temperature from about room temperature to about 100° C. in the presence of an acidic catalyst.

7. A process according to claim 6 wherein the acidic catalyst is hydrogen chloride.

8. A process according to claim 7 wherein the 4H-substituted-1,2,4-triazole is

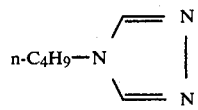

9. A process according to claim 8 wherein the 4H-substituted-1,2,4-triazole is

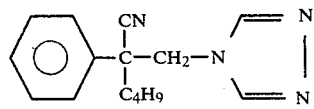

* * * * *